(12) United States Patent
Harada et al.

(10) Patent No.: US 6,653,489 B2
(45) Date of Patent: Nov. 25, 2003

(54) PROCESSES FOR PRODUCING TETRAHYDROPYRANYL-4-SULFONATES AND 4-AMINOTETRAHYDROPYRAN COMPOUNDS

(75) Inventors: Katsumasa Harada, Ube (JP); Shigeyoshi Nishino, Ube (JP); Hidetaka Shima, Ube (JP); Minoru Nishimura, Ube (JP); Kenji Hirotsu, Ube (JP)

(73) Assignee: Ube Industries, Inc., Yamaguchi (JP)

( * ) Notice: Subject to any disclaimer, the term of this patent is extended or adjusted under 35 U.S.C. 154(b) by 0 days.

(21) Appl. No.: 10/148,750

(22) PCT Filed: Dec. 8, 2000

(86) PCT No.: PCT/JP00/08695

§ 371 (c)(1),
(2), (4) Date: Jun. 3, 2002

(87) PCT Pub. No.: WO01/42232

PCT Pub. Date: Jun. 14, 2001

(65) Prior Publication Data

US 2003/0004359 A1 Jan. 2, 2003

(30) Foreign Application Priority Data

Dec. 10, 1999 (JP) .............................. 11-351712
Feb. 16, 2000 (JP) ............................. 2000-38320

(51) Int. Cl.[7] .................................. C07D 309/02
(52) U.S. Cl. ........................................ 549/416
(58) Field of Search ......................... 549/416

(56) References Cited

U.S. PATENT DOCUMENTS 3,669,992 A    6/1972  Stapp
3,759,956 A    9/1973  Stapp
4,288,374 A  * 9/1981  Squire ................ 260/347.91

OTHER PUBLICATIONS

F. Caturla et al, "Preparation and synthetic applications of lithiated vinyl sulfones derived from 3–buten–1–o1 and 4–penten–1–ol", *Tetrahedron*, vol. 53, No. 33, pp. 11449–11464 (1997).
S.V. Ley et al, "Alkylation reactions of anions derived from 2–(benzenesulphonyl) tetrahydropyran and their applications to spiroketal synthesis", *Tetrahedron*, vol. 42, No. 15, pp. 4333–4342.
Grob, et al., Nucleophile Ringöffnung und Fragmentierung von 1–Aza–bicyclo[2.2.0]hexan; Helvetica Chimica Acta, vol. 47, No. 8, 1964, pp. 2145–2154, XP009002588.
Ernst Hanschke, "Zur Kenntnis der Prinsschen Reaktion: über die Reaktion von Allylcarbinol mit Aldehyden und Ketonen", Chem. Ber., vol. 88, No. 7, 1955, pp. 1053–1061, XP009002590.
Heuberger, et al., "Tetrahydropyran–3:4–diol and tetrahydro–2:2:5:5–tetramethylfuran–3:4–diol", J. Chem. Soc., 1952, pp. 910–914, XP009002589.

* cited by examiner

*Primary Examiner*—Joseph K. McKane
*Assistant Examiner*—Golam M M Shameem
(74) *Attorney, Agent, or Firm*—Frishauf, Holtz, Goodman & Chick, P.C.

(57) ABSTRACT

The present invention is to provide a process for producing a tetrahydropyranyl-4-sulfonate which comprises allowing 3-buten-1-ol which is easily available to react with a formaldehyde compound and an organic sulfonic acid, and a process for producing a 4-aminotetrahydropyrane derivative, which is industrially useful, under mild conditions and by a simple and easy method to produce the 4-aminotetrahydropyrane derivative in high yield.

18 Claims, No Drawings

PROCESSES FOR PRODUCING TETRAHYDROPYRANYL-4-SULFONATES AND 4-AMINOTETRAHYDROPYRAN COMPOUNDS

This application is a United States National Phase Application under 35 U.S.C. 371 of International Application No. PCT/JP00/08695 filed Dec.8, 2000.

TECHNICAL FIELD

The present invention relates to a process for producing a tetrahydropyranyl-4-sulfonate and a process for producing a 4-aminotetrahydropyran compound from the tetrahydropyranyl-4-sulfonate. The tetrahydropyranyl-4-sulfonate is a useful compound for introducing a tetrahydropyranyl group into various compounds by substitution of a sulfonyl group, and the 4-aminotetrahydropyran compound is a useful compound as a synthetic intermediate or a starting material for medicines, agricultural chemicals, and the like.

BACKGROUND ART

As a process for producing a tetrahydropyranyl-4-sulfonate from 3-buten-1-ol, there has been known a process for producing it by two steps through a tetra-hydropyran-4-ol, for example, 3-buten-1-ol and formalin are reacted in the presence of sulfuric acid to synthesize the tetrahydropyran-4-ol with a yield of 76% (Chem. Ber., 88, p.1053 (1955)), and then, in the presence of a base, the tetrahydropyran-4-ol and methanesulfonyl chloride are reacted to synthesize a tetrahydropyranyl-4-methanesulfonate with an yield of 35% (J. Chem. Soc., 1952, p.910), and the like.

Also, as a process for producing a 4-aminotetrahydropyran compound, there have been known, for example, a method of contacting an ammonia gas and a hydrogen gas with a tetrahydropyran-4-one in the presence of Raney Nickel (Helv. Chim. Acta, 47, 2145 (1964)), a method of reacting a tetrahydropyran-4-one and an amine in the presence of sodium cyanoborohydride (J. Med. Chem., 37, 565 (1994)), a method of heating a tetrahydropyran-4-one in a mixed solution of water, N,N-dimethylformamide and formic acid (Japanese Provisional Patent Publication No. Hei.11-263764) and the like. However, the tetrahydropyran-4-one is a compound synthesis of which is relatively difficult and is a compound extremely unstable to a base and troublesome in handling since it is ring-opened easily and forms polymers, and there is a problem that an yield of the objective 4-aminotetrahydropyrane compound is low in either of the methods.

On the other hand, there is disclosed a method in which a 4-chlorotetrahydropyrane and ammonia in an autoclave at 200° C. (J. Org. Chem., 36, 522 (1971)), but the reaction conditions thereof are extremely strict and there is a problem of low yield.

An object of the present invention is to provide a process for producing a tetrahydropyranyl-4-sulfonate, which is industrially advantageous, from an easily available 3-buten-1-ol without requiring any complicated operations, with a simple and easy method and which is capable of producing the tetrahydropyranyl-4-sulfonate with one step and high yield.

Also, another object of the present invention is to provide a process for producing a 4-aminotetrahydropyrane compound which is industrially suitable, under mild conditions and by a simple and easy method to produce the 4-aminotetrahydropyrane compound in high yield.

SUMMARY OF THE INVENTION

The present invention relates to a process for producing a tetrahydropyranyl-4-sulfonate which comprises allowing 3-buten-1-ol to react with a formaldehyde derivative and an organic sulfonic acid.

Also, the present invention relates to a process for producing a 4-aminotetrahydropyran compound represented by the following formula (2):

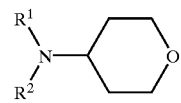

(2)

wherein $R^1$ and $R^2$ each represent a group which does not participate in the reaction; and $R^1$ and $R^2$ may form a ring by bonding to each other, which comprises allowing a tetrahydropyranyl-4-sulfonate to react with an amine represented by the following formula (1):

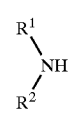

(1)

wherein $R^1$ and $R^2$ have the same meanings as defined above.

BEST MODE FOR CARRYING OUT THE INVENTION

First, a process for producing the tetrahydropyranyl-4-sulfonate of the present invention will be explained.

3-Buten-1-ol to be used as a starting material in the reaction of the present invention is a compound capable of being easily synthesized by dehydration reaction of 1,4-butanediol (for example, Bull. Chem. Soc. Jpn., 54, 1585 (1981)) or a monoepoxidation reaction of butadiene and a subsequent reduction (for example, WO 9936379).

As the formaldehyde derivative to be used in the reaction of the present invention, there may be mentioned an aqueous solution of formaldehyde or a polymer of formaldehyde, and, for example, formalin, paraformaldehyde and trioxane are suitably used.

An amount of the above-mentioned formaldehyde derivative is preferably 1.0 to 5.0-fold moles, more preferably 1.1 to 2.0-fold moles based on the starting material, 3-buten-1-ol (in terms of formaldehyde). These formaldehyde derivatives may be used singly or in combination of two or more.

As the organic sulfonic acid to be used in the reaction of the present invention, there may be mentioned, for example, an alkylsulfonic acid such as methanesulfonic acid, ethanesulfonic acid, etc.; an arylsulfonic acid such as benzenesulfonic acid, p-toluenesulfonic acid, p-chlorobenzenesulfonic acid, p-bromobenzenesulfonic acid, etc.

An amount of the above-mentioned organic sulfonic acid to be used is preferably 1.0 to 5.0-fold moles, more preferably 1.1 to 3.0-fold moles based on the starting material, 3-buten-1-ol.

The reaction of the present invention is carried out in the presence or absence of a solvent. As the solvent to be used, there may be mentioned, for example, water; an aromatic hydrocarbon such as benzene, toluene, xylene, mesitylene, etc.; a halogenated hydrocarbon such as chloroform, dichloroethane, etc.; an organic acid ester such as ethyl acetate, butyl acetate, etc.; an ether such as tetrahydropyrane, diisopropyl ether, etc., and preferably an aromatic hydrocarbon, more preferably, benzene, toluene, and particularly preferably toluene.

An amount of the above-mentioned solvent is preferably 0 to 50 ml, more preferably 0 to 10 ml based on 1 g of 3-buten-1-ol. These solvents may be used singly or in combination of two or more.

The reaction of the present invention is preferably carried out by contacting the starting materials, 3-buten-1-ol, the formaldehyde derivative and the organic sulfonic acid in a liquid phase, and may be carried out by a method in which, for example, under an inert gas atmosphere, 3-buten-1-ol, the formaldehyde derivative and the organic sulfonic acid are mixed and stirred under heating, and the like, under a normal pressure or under a pressure. An order of mixing the above-mentioned compounds is optional, and all are mixed simultaneously, or to either one or a mixture of two kinds, the remaining materials are optionally added stepwisely or simultaneously. A reaction temperature at the time is preferably 10 to 80° C., more preferably 20 to 60° C.

Incidentally, the tetrahydropyranyl-4-sulfonate which is a final product of the above-mentioned reaction can be, for example, purified by a general method such as distillation, recrystallization, column chromatography and the like, after removing the solvent after completion of the reaction.

Next, a process for producing a 4-aminotetrahydropyran compound of the present invention is explained.

The tetrahydropyranyl-4-sulfonate which is used as a starting material for the reaction of the present invention is a compound easily synthesized by allowing 3-buten-1-ol to react with the formaldehyde derivative (for example, formalin) and the organic sulfonic acid as described above.

As the above-mentioned tetrahydropyranyl-4-sulfonate, there may be mentioned, for example, tetrahydropyranyl-4-alkylsulfonate such as tetrahydropyranyl-4-methanesulfonate, tetrahydropyranyl-4-ethanesulfonate, etc.; tetrahydropyranyl-4-arylsulfonate such as tetrahydropyranyl-4-benzenesulfonate, tetrahydropyranyl-4-p-toluenesulfonate, tetrahydropyranyl-4-p-chlorobenzenesulfonate, tetrahydropyranyl-4-p-bromobenzenesulfonate, etc.

The amine to be used in the reaction of the present invention is represented by the above-mentioned formula (1). In the formula (1), $R^1$ and $R^2$ are groups which do not participate in the reaction, and more specifically, they may be the same or different from each other, and represents a hydrogen atom, an alkyl group, a cycloalkyl group, an aralkyl group or an aryl group, each of which may have a substituent(s). Also, $R^1$ and $R^2$ may form a ring by bonding to each other.

As the above-mentioned alkyl group, an alkyl group having 1 to 10 carbon atoms is particularly preferred, and, for example, there may be mentioned a methyl group, an ethyl group, a propyl group (and its isomer), a butyl group (and its isomers), a pentyl group (and its isomers), a hexyl group (and its isomers), a heptyl group (and its isomers), an octyl group (and its isomers), a nonyl group (and its isomers) and a decyl group (and its isomers).

As the above-mentioned cycloalkyl group, a cycloalkyl group having 3 to 7 carbon atoms is particularly preferred, and there may be mentioned, for example, a cyclopropyl group, a cyclobutyl group, a cyclopentyl group, a cyclohexyl group and a cycloheptyl group.

As the above-mentioned aralkyl group, an aralkyl group having 7 to 10 carbon atoms is particularly preferred, and there may be mentioned, for example, a benzyl group, a phenethyl group (and its isomers), a phenylpropyl group (and its isomers) and a phenylbutyl group (and its isomers).

As the above-mentioned aryl group, an aryl group having 6 to 14 carbon atoms is particularly preferred, and there may be mentioned, for example, a phenyl group, a p-tolyl group, a naphthyl group and an anthranyl group.

The above-mentioned alkyl group, cycloalkyl group, aralkyl group or aryl group may have a substituent(s). As the substituent(s), there may be mentioned at least one selected from a substituent formed through a carbon atom, a substituent formed through an oxygen atom, a substituent formed through a nitrogen atom, and a halogen atom.

As the above-mentioned substituent formed through a carbon atom, there may be mentioned, for example, an alkyl group such as a methyl group, an ethyl group, a propyl group, etc.; an aralkyl group such as a benzyl group, etc.; an aryl group such as a phenyl group, etc.; and a cyano group.

As the above-mentioned substituent formed through an oxygen atom, there may be mentioned, for example, an alkoxy group such as a methoxy group, an ethoxy group, a propoxy group, a butoxy group, a benzyloxy group, etc.; an aryloxy group such as a phenoxy group, etc.; an acyloxy group such as an acetoxy group, a benzoyloxy group, etc.

As the above-mentioned substituent formed through a nitrogen atom, there may be mentioned, for example, a nitro group; and an amino group.

As the above-mentioned halogen atom, there may be mentioned a fluorine atom, a chlorine atom, a bromine atom, and an iodine atom.

As the amine to be used in the reaction of the present invention, an amine itself may be used, and in the case of an amine having a low boiling point at atmospheric pressure, it is preferably used as an aqueous solution or an alcoholic solution, which is easy to handle. A concentration thereof is preferably 1 to 90% by weight, more preferably 3 to 60% by weight.

An amount of the above-mentioned amine is preferably 1 to 60-fold moles, more preferably 3 to 40-fold moles based on an amount of the starting material, tetrahydropyranyl-4-sulfonate.

The reaction of the present invention is carried out in the presence or absence of a solvent. As the solvent to be used, there may be mentioned, for example, water; an amide such as N,N-dimethylformamide, etc.; an urea such as N,N-dimethylimidazolidinone, etc.; an alcohol such as methanol, ethanol, isopropyl alcohol, t-butyl alcohol, etc.; an aromatic hydrocarbon such as benzene, toluene, xylene, mesitylene, etc.; a halogenated hydrocarbon such as methylene chloride, chloroform, dichloroethane, etc.; and preferably water and an alcohol, more preferably water, methanol and ethanol.

An amount of the above-mentioned solvent is preferably 0 to 50-fold weight, more preferably 0 to 20-fold weight based on the starting material, tetrahydropyranyl-4-sulfonate. These solvents may be used singly or in combination of two or more.

The reaction of the present invention is preferably carried out by contacting a tetrahydropyranyl-4-sulfonate and an amine in a liquid phase, for example, it is carried out by a method in which a tetrahydropyranyl-4-sulfonate and an amine are mixed under an inert gas atmosphere, and stirred under heating and the like, under atmospheric pressure or under pressure. A reaction temperature at that time is preferably 40 to 180° C., more preferably 50 to 130° C.

Also, if necessary, by adding an inorganic base or an organic base in the system, reactivity may be controlled.

Incidentally, the final product, the 4-aminotetrahydropyrane derivative is, for example, separated and purified after completion of the reaction by a conventional method such as distillation, recrystallization, column chromatography and the like.

EXAMPLES

Next, the present invention will be explained in more detail by referring to Examples, but the scope of the present invention is not limited by these.

Example 1

Into 10 ml of a flask made of glass equipped with a stirring device, a thermometer and a dropping funnel were charged 1.00 g (13.9 mmol) of 3-buten-1-ol and 1.35 g (16.6 mmol) of a 37% by weight aqueous formalin solution (available from Wako Junyaku Co.), and under nitrogen atmosphere, 2.66 g (27.7 mmol) of methanesulfonic acid was gradually added dropwise under stirring and the resulting mixture was reacted at 25° C. for 3 hours. After completion of the reaction, the resulting reaction mixture was analyzed by high performance liquid chromatography and it was found that tetrahydropyranyl-4-methanesulfonate was formed in an amount of 1.65 g (yield: 66%).

Example 2

In a similar reaction apparatus used in Example 1 were added 1.00 g (13.9 mmol) of 3-buten-1-ol, 0.50 g (15.3 mmol) of 92% by weight paraformaldehyde (available from Mitsui Toatsu Chemical Co.) and 5 ml of toluene, and under nitrogen atmosphere, 3.99 g (41.5 mmol) of methanesulfonic acid was gradually added dropwise while stirring and the resulting mixture was reacted at 25° C. for 3 hours. After completion of the reaction, the resulting reaction mixture was analyzed by high performance liquid chromatography and it was found that 2.15 g (yield: 86%) of tetrahydropyranyl-4-methanesulfonate was formed.

Example 3

In a similar reaction apparatus used in Example 1 were added 1.00 g (13.9 mmol) of 3-buten-1-ol, 0.50 g (5.6 mmol; which corresponds to 16.8 mmol in terms of formaldehyde) of trioxane and 5 ml of toluene, and under nitrogen atmosphere, 2.66 g (27.7 mmol) of methanesulfonic acid was gradually added dropwise while stirring and the resulting mixture was reacted at 25° C. for 3 hours. After completion of the reaction, the resulting reaction mixture was analyzed by high performance liquid chromatography and it was found that 2.13 g (yield: 85%) of tetrahydropyranyl-4-methanesulfonate was formed.

Example 4

Into 50 ml of a flask made of glass equipped with a stirring device and a thermometer were charged 1.00 g (13.9 mmol) of 3-buten-1-ol, 0.50 g (15.3 mmol) of 92% by weight paraformaldehyde (available from Mitsui Toatsu Chemical Co.), 5.23 g (27.5 mmol) of p-toluenesulfonic acid monohydrate and 5 ml of toluene, and the resulting mixture was reacted under nitrogen atmosphere while stirring at 55° C. for 2 hours. After completion of the reaction, the resulting reaction mixture was analyzed by high performance liquid chromatography and it was found that 2.32 g (yield: 65%) of tetrahydropyranyl-4-p-toluenesulfonate was formed.

Example 5

Synthesis of tetrahydropyranyl-4-methanesulfonate

Into 300 ml of a flask made of glass equipped with a stirring device, a thermometer and a dropping funnel were charged 40.0 g (0.55 mol) of 3-buten-1-ol, 21.6 g (0.66 mol) of 92% by weight paraformaldehyde (available from Mitsui Toatsu Chemical Co.) and 200 ml of toluene, and under nitrogen atmosphere, 85.3 g (0.89 mol) of methanesulfonic acid was gradually added dropwise under stirring and the resulting mixture was reacted at 55° C. for 2 hours. After completion of the reaction, 100 ml of a brine solution was added to the resulting reaction mixture and the mixture was extracted with 200 ml of ethyl acetate three times. Then, the organic layer was separated, washed twice with 50 ml of a saturated aqueous potassium carbonated solution and dried over anhydrous magnesium sulfate. After filtration, the filtrate was concentrated under reduced pressure to obtain 84.3 g (yield: 73%) of tetrahydropyranyl-4-methanesulfonate with a purity of 86% (areal percentage according to high performance liquid chromatography) as a pale yellowish solid.

Physical properties of tetrahydropyranyl-4-methanesulfonate were CI-MS (m/e); 181 (M+1), $^1$H-NMR (CDCl$_3$); 1.88 ppm (2H, m), 2.04 ppm (2H, m), 3.04 ppm (3H, s), 3.55 ppm (2H, m), 3.95 ppm (2H, m), 4.90 ppm (1H, m).

Example 6

Synthesis of tetrahydropyranyl-4-p-toluenesulfonate

Into 200 ml of a flask made of glass equipped with a stirring device, a thermometer and a dropping funnel were charged 20.0 g (0.28 mol) of 3-buten-1-ol, 10.8 g of 92% by weight paraformaldehyde (available from Mitsui Toatsu Chemical Co.) and 100 ml of toluene, and under nitrogen atmosphere, 84.4 g (0.44 mol) of p-toluenesulfonic acid monohydrate was gradually added dropwise under stirring and the resulting mixture was reacted at 55° C. for 3 hours. After completion of the reaction, 50 ml of a saturated brine solution was added to the resulting reaction mixture and the mixture was extracted with 100 ml of ethyl acetate three times. Then, the organic layer was separated, washed twice with 50 ml of a saturated aqueous potassium carbonated solution and dried over anhydrous magnesium sulfate. After filtration, the filtrate was concentrated under reduced pressure to obtain 49.4 g (yield: 64%) of tetrahydropyranyl-4-p-toluenesulfonate with a purity of 93% (areal percentage according to gas chromatography) as a white solid.

Physical properties of tetrahydropyranyl-4-p-toluenesulfonate were CI-MS (m/e); 257 (M+1) $^1$H-NMR (CDCl$_3$); 1.7 to 1.9 ppm (4H, m), 2.45 ppm (3H, s), 3.47 ppm (2H, m), 3.87 ppm (2H, m), 4.69 ppm (1H, m), 7.34 ppm (2H, d, J=8.2 Hz), 7.80 ppm (2H, d, J=8.2 Hz).

Example 7

Into an autoclave made of stainless having an inner volume of 10 ml and equipped with a stirring device and a thermometer were charged 0.57 g (2.1 mmol) of tetrahydropyranyl-4-p-toluenesulfonate synthesized in Example 6 and having a purity of 93% and 5.6 g (62 mmol) of 50% by weight aqueous dimethylamine solution (available from Katayama Kagaku Co.), and the mixture was reacted at 70° C. for 4 hours. After completion of the reaction, the resulting reaction mixture was analyzed by high performance liquid chromatography (an internal standard method) and it was found that 0.18 g (yield: 66%) of 4-dimethylaminotetrahydropyrane was formed.

Example 8

Into a similar device as in Example 7 were charged 1.05 g (5.0 mmol) of tetrahydropyranyl-4-methanesulfonate synthesized in Example 5 and having a purity of 86% and 9.0 g (100 mmol) of 50% by weight aqueous dimethylamine solution (available from Katayama Kagaku Co.), and the mixture was reacted at 90° C. for 5 hours. After completion of the reaction, the resulting reaction mixture was analyzed by gas chromatography (an internal standard method) and it was found that 0.38 g (yield: 59%) of 4-dimethylaminotetrahydropyrane was formed.

Example 9

In an autoclave made of stainless having an inner volume of 500 ml and equipped with a stirring device and a thermometer were charged 50.0 g (0.24 mmol) of tetrahydropyranyl-4-methanesulfonate synthesized in Example 5 and having a purity of 86% and 400.0 g (4.44 mol) of 50% by weight aqueous dimethylamine solution (available from Katayama Kagaku Co.), and the mixture was reacted at 70° C. for 5 hours. After completion of the reaction, the resulting reaction mixture was transferred into a flask made of glass having a volume of 100 ml equipped with a reflux condenser and a cooling trap (cooled to −20° C. by dry ice/ethanol) and a temperature of the reaction mixture was raised to 50 to 110° C. under stirring, so that unreacted dimethylamine was recovered in the cooling trap (a recovered amount of dimethylamine was 130 g). Thereafter, the reaction mixture was cooled to room temperature, made acidic by adding 25 ml of conc. Hydrochloric acid (pH=1), and then, washed three times with each 100 ml of chloroform. Then, 30 ml of 8 mol/l aqueous sodium hydroxide solution was added to the aqueous layer to make the solution basic (pH=11), and the resulting mixture was extracted three times with each 100 ml of methylene chloride and the resulting organic layer was dried over anhydrous magnesium sulfate. After filtration, the filtrate was concentrated under reduced pressure, and then, according to distillation under reduced pressure (83 to 85° C., 50 mmHg), 14.6 g (yield: 47%) of 4-dimethylaminotetrahydropyrane having a purity of 99% (areal percentage according to gas chromatography) as a colorless liquid.

Physical properties of 4-dimethylaminotetrahydropyrane were CI-MS (m/e); 130 (M+1) $^1$H-NMR (CDCl$_3$, δ (ppm)); 1.53 (2H, dt, J=4.8, 11.7 Hz), 1.75 (2H, dt, J=2.1, 11.7 Hz), 2.25 to 2.31 (7H, m), 3.36 (2H, dt, J=2.1, 11.7 Hz), 4.01 (2H, dt, J=4.5, 11.7 Hz).

Comparative Example 1

Into a reaction device similar to that used in Example 9 were charged 50.0 g (0.5 mol) of tetrahydropyran-4-one, 180.0 g (2.0 mol) of 50% by weight aqueous dimethylamine solution and 20 g (9 mmol in terms of a palladium atom) of 5% by weight Pd/C, and the mixture was reacted at a hydrogen pressure of 0.2 to 0.4 MPa at 50° C. for 7 hours and further at 70° C. for 4 hours. After completion of the reaction, the resulting reaction mixture was cooled to room temperature and the catalyst was filtered off by Celite, and the filtrate was made acidic (pH=1) by adding 60 ml of conc. sulfuric acid and then washed successively with 200 ml of 2-butanol twice and 200 ml of chloroform twice. Then, 130 g of potassium hydroxide was added to the aqueous layer to make the solution basic (pH=11), the aqueous layer was extracted three times with each 300 ml of ethyl acetate and the resulting organic layer was dried over anhydrous magnesium sulfate. After filtration, the organic layer was concentrated under reduced pressure, and then, by distillation under reduced pressure (83 to 85° C., 50 mmHg), 12.4 g (yield: 19%) of 4-dimethylaminotetrahydropyrane with a purity of 99% (areal percentage according to gas chromatography) as a colorless liquid.

Example 10

Into a device similar to that used in Example 7 were charged 1.05 g (5.0 mmol) of tetrahydropyranyl-4-methanesulfonate synthesized in Example 5 and having a purity of 86% and 1.28 g (15.0 mmol) of piperidine, and the mixture was reacted at 100° C. for 4 hours. After completion of the reaction, 1.0 ml of 8 mol/l aqueous sodium hydroxide solution and 2.0 ml of water were added to the resulting reaction mixture to make the mixture basic (pH=11), the resulting mixture was extracted twice with each 30 ml of chloroform and the extract was dried over anhydrous magnesium sulfate. After filtration, the extract was concentrated under reduced pressure to obtain 0.74 g (yield: 72%) of 4-piperidinotetrahydropyrane having a purity of 82% (areal percentage according to gas chromatography) as a yellowish liquid.

Physical properties of 4-piperidinotetrahydropyrane were CI-MS (m/e); 169 (M+1) $^1$H-NMR (CDCl$_3$, δ (ppm)); 1.42 to 1.77 (10H, m), 2.37 to 2.46 (1H, m), 2.51 (4H, t, J=5.7 Hz), 3.36 (2H, dt, J=2.4, 12.0 Hz), 4.01 (2H, dd, J=4.5, 11.1 Hz).

Example 11

Into an autoclave made of stainless having an inner volume of 500 ml and equipped with a stirring device and a thermometer were charged 50.0 g (0.24 mol) of tetrahydropyranyl-4-methanesulfonate synthesized in Example 5 and having a purity of 86% and 400.0 g (5.15 mol) of 40% by weight aqueous methylamine solution (available from Katayama Kagaku Co.), and the mixture was reacted at 70° C. for 3 hours. After completion of the reaction, the resulting reaction mixture was transferred into 1000 ml of a flask made of glass equipped with a reflux condenser and a cooling trap (cooled to −20° C. by dry ice/methanol), and a temperature of the reaction mixture was raised to 50 to 110° C. under stirring, so that unreacted methylamine was recovered in the cooling trap (a recovered amount of methylamine was 57 g). Thereafter, the reaction mixture was cooled to room temperature, made acidic by adding 25 ml of conc. Hydrochloric acid (pH=1), and then, washed three times with each 100 ml of chloroform. Then, 40 ml of 8 mol/l aqueous sodium hydroxide solution was added to the aqueous layer to make the solution basic (pH=9), and the resulting mixture was extracted three times with each 100 ml of chloroform and the resulting organic layer was dried over anhydrous magnesium sulfate. After filtration, the filtrate was concentrated under reduced pressure, and then, according to distillation under reduced pressure (78 to 85° C., 50 mmHg), 11.0 g (yield: 36%) of 4-methylaminotetrahydropyrane having a purity of 90% (areal percentage according to gas chromatography) as a colorless liquid.

Physical properties of 4-methylaminotetrahydropyrane were CI-MS (m/e); 115 (M+1) $^1$H-NMR (CDCl$_3$, δ (ppm)); 0.8 to 1.2 (1H, brs), 1.37 (2H, dt, J=4.8, 11.7 Hz), 1.81 to 1.87 (2H, m), 2.44 (3H, s), 2.51 to 2.61 (1H, m), 3.40 (2H, dt, J=2.4, 11.7 Hz), 3.98 (2H, dt, J=3.6, 11.7 Hz).

Example 12

Into a similar device as that used in Example 7 were charged 0.21 g (1.0 mmol) of tetrahydropyranyl-4-methanesulfonate synthesized in Example 5 and having a purity of 86% and 5.0 ml (10 mmol) of 2 mol/l methylamine ethanol solution, and the mixture was reacted at 100° C. for 5 hours. After completion of the reaction, the resulting mixture was analyzed by gas chromatography (internal standard method), it was found that 0.047 g (yield: 41%) of 4-methylaminotetrahydropyrane was formed.

Example 13

Into a similar device as that used in Example 7 were charged 0.21 g (1.0 mmol) of tetrahydropyranyl-4-methanesulfonate synthesized in Example 5 and having a purity of 86% and 5.0 ml (10 mmol) of 2 mol/l ammonia ethanol solution, and the mixture was reacted at 130° C. for 10 hours. After completion of the reaction, the resulting mixture was analyzed by gas chromatography (internal standard method), it was found that 0.083 g (yield: 83%) of 4-aminotetrahydropyrane was formed. Then, the mixture was concentrated under reduced pressure to obtain 0.020 g of 4-aminotetrahydropyrane having a purity of 99% (areal percentage according to gas chromatography) as a pale yellowish liquid.

Physical properties of 4-aminotetrahydropyrane were CI-MS (m/e); 102 (M+1) $^1$H-NMR (CDCl$_3$, δ (ppm)); 1.31 to 1.45 (4H, m), 1.74 to 1.80 (2H, m), 2.80 to 2.90 (1H, m), 3.39 (2H, dt, J=2.4, 12.6 Hz), 3.95 (2H, dt, J=3.3, 11.4 Hz).

Example 14

Into a similar device to that used in Example 7 were charged 1.38 g (5.0 mmol) of tetrahydropyranyl-4-p-toluenesulfonate synthesized in Example 6 and having a purity of 93% and 3.18 g (26.0 mmol) of benzylmethylamine, and the mixture was reacted at 70° C. for 4 hours and further at 90° C. for 5 hours. After completion of the reaction, the resulting reaction mixture was concentrated under reduced pressure and purified by silica gel column chromatography (Filler: Wako gel C-200 (available from Wako Junyaku Co.), Eluent: chloroform/methanol (=9/1 (volume ratio)) to obtain 0.72 g (yield: 70%) of 4-benzylmethylaminotetrahydropyrane having a purity of 90% (areal percentage according to high performance liquid chromatography) as a pale yellowish liquid.

Physical properties of 4-benzylmethylaminotetrahydropyrane were CI-MS (m/e); 206 (M+1) $^1$H-NMR (CDCl$_3$, δ (ppm)); 1.61 to 1.84 (4H, m), 2.20 (3H, s), 2.56 to 2.69 (1H, m), 3.32 to 3.41 (2H, m), 3.58 (2H, s), 4.02 to 4.68 (2H, m), 7.22 to 7.36 (5H, m).

Example 15

Into a similar device as that used in Example 7 were charged 1.05 g (5.0 mmol) of tetrahydropyranyl-4-methanesulfonate synthesized in Example 5 and having a purity of 86% and 1.61 g (15.0 mmol) of N-methylaniline, and the mixture was reacted at 100° C. for 4 hours. After completion of the reaction, to the resulting reaction mixture were added 1.0 ml of 8 mol/l aqueous sodium hydroxide solution and 2.0 ml of water to make the mixture basic, the mixture was washed twice with each 30 ml of chloroform and the organic layer was dried over anhydrous magnesium sulfate. After filtration, the filtrate was concentrated under reduced pressure, and purified by silica gel column chromatography (Filler: Wako gel C-200 (available from Wako Junyaku Co.), Eluent: toluene/ethyl acetate (=3/1 (volume ratio)) to obtain 0.16 g (yield: 17%) of 4-N-methylanilinotetrahydropyrane having a purity of 99% (areal percentage according to high performance liquid chromatography) as a reddish liquid.

Physical properties of 4-N-methylanilinotetrahydropyrane were CI-MS (m/e); 192 (M+1) $^1$H-NMR (CDCl$_3$, δ (ppm)); 1.66 to 1.92 (4H, m), 2.79 (3H, s), 3.47 (2H, dt, J=2.1, 11.7 Hz), 3.77 to 3.86 (1H, m), 4.06 (2H, dd, J=4.8, 11.7 Hz), 6.73 (1H, t, J=7.2 Hz), 6.82 (2H, d, J=8.1 Hz), 7.21 to 7.23 (2H, m).

Utilizability in Industry

According to the present invention, a process for producing tetrahydropyranyl-4-sulfonate can be provided, which is industrially useful, from an easily available 3-buten-1-ol without requiring any complicated operation, with a simple and easy method and with a single step to form tetrahydropyranyl-4-sulfonate in high yield.

Also, according to the present invention, a process for producing a 4-aminotetrahydropyrane derivative, which is industrially useful, from tetrahydropyranyl-4-sulfonate which can be easily synthesized under mild conditions and a simple and easy method to produce 4-aminotetrahydropyrane derivative in high yield.

What is claimed is:

1. A process for producing a tetrahydropyranyl-4-sulfonate which comprises reacting 3-buten-1-ol with a formaldehyde compound and an organic sulfonic acid.

2. The process for producing the tetrahydropyranyl-4-sulfonate according to claim 1, wherein the formaldehyde compound is at least one selected from the group consisting of an aqueous formaldehyde solution, paraformaldehyde and trioxane.

3. The process for producing the tetrahydropyranyl-4-sulfonate according to claim 1, wherein the formaldehyde compound is used in an amount of 1.0 to 5.0-fold mole based on an amount of 3-buten-1-ol.

4. The process for producing the tetrahydropyranyl-4-sulfonate according to claim 1, wherein the organic sulfonic acid is at least one selected from the group consisting of methanesulfonic acid, ethanesulfonic acid, benzenesulfonic acid, p-toluenesulfonic acid, p-chlorobenzenesulfonic acid and p-bromobenzenesulfonic acid.

5. The process for producing the tetrahydropyranyl-4-sulfonate according to claim 1, wherein the organic sulfonic acid is used in an amount of 1.0 to 5.0-fold moles based on an amount of 3-buten-1-ol.

6. The process for producing the tetrahydropyranyl-4-sulfonate according to claim 1, wherein the reaction is carried out in an inert gas atmosphere by mixing 3-buten-1-ol, the formaldehyde compound and organic sulfonic acid at atmospheric pressure or under pressure at 10 to 80° C.

7. The process for producing the tetrahydropyranyl-4-sulfonate according to claim 2, wherein the reaction is carried out in an inert gas atmosphere by mixing 3-buten-1-ol, the formaldehyde compound and organic sulfonic acid at atmospheric pressure or under pressure at 10 to 80° C.

8. The process for producing the tetrahydropyranyl-4-sulfonate according to claim 3, wherein the reaction is carried out in an inert gas atmosphere by mixing 3-buten-1-ol, the formaldehyde compound and organic sulfonic acid at atmospheric pressure or under pressure at 10 to 80° C.

9. The process for producing the tetrahydropyranyl-4-sulfonate according to claim 4, wherein the reaction is carried out in an inert gas atmosphere by mixing 3-buten-1-ol, the formaldehyde compound and organic sulfonic acid at atmospheric pressure or under pressure at 10 to 80° C.

10. The process for producing the tetrahydropyranyl-4-sulfonate according to claim 5, wherein the reaction is carried out in an inert gas atmosphere by mixing 3-buten-1-ol, the formaldehyde compound and organic sulfonic acid at atmospheric pressure or under pressure at 10 to 80° C.

11. The process for producing the tetrahydropyranyl-4-sulfonate according to claim 1, wherein the formaldehyde compound is an aqueous formaldehyde solution.

12. The process for producing the tetrahydropyranyl-4-sulfonate according to claim 1, wherein the formaldehyde compound is paraformaldehyde.

13. The process for producing the tetrahydropyranyl-4-sulfonate according to claim 1, wherein the formaldehyde compound is trioxane.

14. The process for producing the tetrahydropyranyl-4-sulfonate according to claim 1, wherein the formaldehyde compound is used in an amount of 1.1 to 2.0-fold moles based on an amount of 3-buten-1-ol.

15. The process for producing the tetrahydropyranyl-4-sulfonate according to claim 1, wherein the organic sulfonic acid is used in an amount of 1.1 to 3.0-fold moles based on an amount of 3-buten-1-ol.

16. The process for producing the tetrahydropyranyl-4-sulfonate according to claim 1, wherein the reaction is carried out by mixing 3-buten-1-ol, the formaldehyde compound and organic sulfonic acid at atmospheric pressure or under pressure at 20 to 60° C.

17. The process for producing the tetrahydropyranyl-4-sulfonate according to claim 1, wherein the reaction is carried out in the presence of a solvent selected from the group consisting of an aromatic hydrocarbon, a halogenated hydrocarbon and an organic acid ester in an amount of 0 to 50 ml based on 1 g of 3-buten-1-ol.

18. The process for producing the tetrahydropyranyl-4-sulfonate according to claim 1, wherein the reaction is carried out in the presence of an aromatic hydrocarbon selected from the group consisting of benzene, toluene xylene and mesitylene in an amount of 0 to 10 ml based on 1 g of 3-buten-1-ol.

* * * * *